(12) United States Patent
Carpenter et al.

(10) Patent No.: US 10,751,479 B2
(45) Date of Patent: Aug. 25, 2020

(54) NEEDLE COVER ASSEMBLY

(71) Applicant: SHL MEDICAL AG, Zug (CH)

(72) Inventors: Lucas Carpenter, New Taipei (TW); Stephan Mueller, Taoyan (TW)

(73) Assignee: SHL MEDICAL AG, Zug (CH)

( * ) Notice: Subject to any disclaimer, the term of this patent is extended or adjusted under 35 U.S.C. 154(b) by 149 days.

(21) Appl. No.: 15/517,870

(22) PCT Filed: Sep. 15, 2015

(86) PCT No.: PCT/EP2015/071052
§ 371 (c)(1),
(2) Date: Apr. 7, 2017

(87) PCT Pub. No.: WO2016/055241
PCT Pub. Date: Apr. 14, 2016

(65) Prior Publication Data
US 2017/0304556 A1    Oct. 26, 2017

(30) Foreign Application Priority Data
Oct. 8, 2014 (SE) ........................... 1451198

(51) Int. Cl.
*A61M 5/32* (2006.01)
*A61M 5/00* (2006.01)
(Continued)

(52) U.S. Cl.
CPC .......... *A61M 5/3202* (2013.01); *A61M 5/002* (2013.01); *A61M 5/326* (2013.01);
(Continued)

(58) Field of Classification Search
CPC .............. A61M 5/3202; A61M 5/3245; A61M 5/3271; A61M 5/3272; A61M 2005/3267; A61M 5/5086
See application file for complete search history.

(56) References Cited

U.S. PATENT DOCUMENTS 4,664,259 A * 5/1987 Landis ................ A61M 5/3216
206/364
4,693,708 A * 9/1987 Wanderer ............... A61B 5/153
604/198
(Continued)

FOREIGN PATENT DOCUMENTS

| EP | 0409180 A1 | 1/1991 |
|---|---|---|
| WO | 03045480 A1 | 6/2003 |
| WO | 2006082350 A1 | 8/2006 |
| WO | 2008067467 A2 | 6/2008 |
| WO | 2008118170 A1 | 10/2008 |

*Primary Examiner* — Kami A Bosworth
*Assistant Examiner* — Leah J Swanson
(74) *Attorney, Agent, or Firm* — McDonnell Boehnen Hulbert & Berghoff LLP (57) ABSTRACT

A needle cover assembly can be used with a medicament delivery device, wherein said needle cover assembly is disposable and comprises a retainer element connectable to a medicament container holder; a hub having a longitudinal axis and comprising a double pointed injection needle with a proximal needle end and a distal needle end, wherein the proximal needle end projects a distance from the hub along the longitudinal axis, and a shield covering at least the proximal needle end and a portion of the hub. Said shield comprises a detachable element, that the shield is attached to the hub when said detachable element is attached to the shield, corresponding to an untampered state, and that the shield is released and is telescopically movable in relation to the hub along the longitudinal axis when said detachable element is detached from the shield corresponding to an activated state.

19 Claims, 4 Drawing Sheets

(51) Int. Cl.
*A61M 5/50* (2006.01)
*A61M 5/31* (2006.01)

(52) U.S. Cl.
CPC ........ *A61M 5/3245* (2013.01); *A61M 5/3272* (2013.01); *A61M 5/3286* (2013.01); *A61M 5/5086* (2013.01); *A61M 5/50* (2013.01); *A61M 2005/3103* (2013.01); *A61M 2005/3118* (2013.01); *A61M 2005/3121* (2013.01); *A61M 2005/3247* (2013.01); *A61M 2005/3267* (2013.01)

(56) References Cited

U.S. PATENT DOCUMENTS

| | | | | |
|---|---|---|---|---|
| 8,282,609 B2 * | 10/2012 | Weston | ................. | A61M 5/326 604/192 |
| 2012/0041368 A1 * | 2/2012 | Karlsson | ............... | A61M 5/326 604/111 |
| 2012/0277685 A1 * | 11/2012 | Limaye | ............... | A61M 5/3243 604/192 |

* cited by examiner

NEEDLE COVER ASSEMBLY

CROSS REFERENCE TO RELATED APPLICATIONS

The present application is a U.S. National Phase Application pursuant to 35 U.S.C. § 371 of International Application No. PCT/EP2015/071052 filed Sep. 15, 2015, which claims priority to Swedish Patent Application No. 1451198-4, filed Oct. 8, 2014. The entire disclosure contents of these applications are herewith incorporated by reference into the present application.

TECHNICAL AREA

The present invention relates to a needle cover assembly to be used with a medicament delivery device,

BACKGROUND OF INVENTION

Manual disposable syringe based devices for administration of liquid medicament are well known and frequently used for subcutaneous injections, in health care environments as well as for self-administration. Typically, a medicament delivery device is loaded with a cartridge containing a liquid drug, after which a disposable needle assembly comprising a double sided injection needle is applied onto the delivery device so that one needle end penetrates the cartridge and contacts its content. The medicament can thereafter be delivered by means of injection and the needle assembly is removed and discarded after use.

Needle assemblies are delivered in a sterile package that may be in the form of an outer cap arranged with a protective film to be removed before use. It is known to provide a further safety protective device covering the injection needle comprising telescopic sleeves which can slide into each other for exposing the needle during injection while covering the needle in neutral state, i.e. when not used for injection procedure. Such safety devices ensure that accidental and possibly dangerous needle sticks are avoided. Examples of safety devices for injection needles are described e.g. in EP0409180, U.S. Ser. No. 10/307,054 and U.S. Ser. No. 09/870,276.

It is an object of the present invention to provide an improved safety device for injection needles.

BRIEF DESCRIPTION OF INVENTION

In order to achieve the object of the invention, a needle cover assembly for a medicament delivery device according to independent claim 1 is provided.

Further aspects, improvements and variations are disclosed in the dependent claims, the figures and the description.

In the present application, when the term "distal" is used, this refers to the direction pointing away from the dose delivery site, i.e. a human body. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

According to one embodiment, the needle cover assembly comprises a shield covering a hub holding a double pointed injection needle, said shield and hub each having a generally cylindrical hollow shape and being concentric about a longitudinal axis. The shield comprises a detachable element, wherein the shield is attached to the hub when the detachable element is attached to the shield, corresponding to an untampered state, i.e. prior to use, and that the shield is released and is telescopically movable in relation to the hub along the longitudinal axis when said detachable element is detached from the shield corresponding to an activated state, i.e. a state wherein the device is ready for injection procedure.

The assembly is delivered to a user in the untampered state wherein the shield fully covers the length of the hub and the needle respectively. In this state the shield has the function of a protective cap providing a sterile inner environment. In order to prepare the assembly for an injection, i.e. and getting it ready for use, the detachable element is removed from the shield whereby the shield becomes telescopically movable along the longitudinal axis in relation to the hub which holds the needle. Said needle can hereby be exposed by pushing the shield in a distal direction thus collapsing the assembly leading to that the needle is uncovered so that the assembly can be used for injection of medicament. In a neutral state the shield will automatically move to a position where the proximal needle end is covered.

This means removing the detachable element leads to that the shield is transformed from a protective cap into a needle safety device, also referred to as needle safety guard. Consequently, one and the same component is arranged to perform two functions.

Such an integrated needle shield, i.e. a shield that functions as both a protective cap in the untampered state and as a needle safety guard in an active state, provides many advantages. For example it leads to a reduced number of components as no extra external sterile package is required, and thereby also to less waste. Also, the assembly will be easier to produce, requires less material and therefore both manufacturing costs and sales price may be lowered. The user experience will also be improved thanks to that a lesser number of parts must be handled, and further the needle shield is more compact compared to standard variants.

In one embodiment the detachable element is an integral portion of the shield arranged on the shield with a removable portion provided with at least one tearable or breakable groove enabling peeling off the detachable element from the shield. A grippable pull tab may be provided for simplifying peeling manoeuver, wherein said pull tab may be connected to the removable portion.

The shield has a generally cylindrical hollow shape with one distal open end and an opposite proximal end being partially closed and comprising a central opening. When in untampered state the distal open end is sealed e.g. with a film or a label, and the central opening is blocked with a needle seal. Thus, in untampered state the shield works as a protective cap which protects the hub and the needle from contamination and provides an inner sterile environment.

When transforming the shield from a protective cap to a needle safety guard, the film may for instance firstly be removed uncovering the distal open end of the shield. This exposes both the distal end of the hub and the distal needle end respectively. The distal end of the hub is arranged with a retainer element for attachment of the needle cover assembly to a medicament delivery device holding a cartridge with liquid medicament. The retainer element may be any conventional connection including e.g. luer lock, bayonet or threaded connection. Subsequently the needle cover assembly is attached onto the medicament delivery device, which will also lead to that the distal end of the injection needle penetrates a septum of the cartridge and contacts the liquid medicament therein. Thereafter, the detachable element of the shield is peeled off and the needle seal removed whereby the shield adapts the function of a needle safety guard. It is understood that the procedure for transforming the shield may be done in another order and that the above procedure is only an example.

The needle cover assembly comprises a resilient element such as a helical spring located between the hub and the shield, arranged to urge the two components apart, i.e. urging them in opposite directions. In activated state the shield is urged by the resilient element to automatically adopt a position where it covers the proximal end of the injection needle and prevents unintentional sticks/injuries. Pushing the shield in a distal direction tightens the helical spring and results in collapse of the device whereupon the needle extends through the central opening at the proximal front portion of the shield. This manoeuver permits injection procedure.

In one embodiment the removable portion of the shield is integral with the needle seal. In such an exemplary embodiment the needle seal is also designed with a pull tab so that peeling is initiated by pulling the pull tab and thereby firstly removing the needle shield to expose the central opening and subsequently in a continuous movement proceed with peeling off the removable portion which is integral with the shield. This solution provides the advantage of a simple and quick transformation procedure and fast opening of the needle cover assembly.

It is understood that "transformation procedure" herein refers to the procedure of removing the removable portion of the shield resulting in that the remaining shield portion becomes movable in relation to the inner hub thus transforming the shield from a protective cap into a needle safety device, also referred to as needle safety guard.

In another embodiment the removable portion element is separate from the needle seal and the pull tab is situated directly in connection to the detachable element, for instance as a projection of the removable portion on the shield. In such an exemplary embodiment the needle seal is removed in one step and peeling off the removable portion is done in another separate step.

In an activated state the shield and the hub are telescopically movable in relation to each other and are engaged with each other by means of a guiding system where the shield is guided along the outside surface of the hub and is movable in a longitudinal direction in relation to said hub. This ensures a predictable and stable movement of the assembly during use, and certain safety aspects are also provided by means of the guiding system. For instance the guiding system is arranged with a stopping edge which prevents the shield from sliding out of contact with the hub before injection. Further, the guiding system is designed with a safety locking element which provides the function of locking the shield in a position where it fully covers the proximal needle end after injection is completed. The needle cover assembly can thereby be discarded without the risk that the needle is exposed causing injuries to persons handling the waste.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
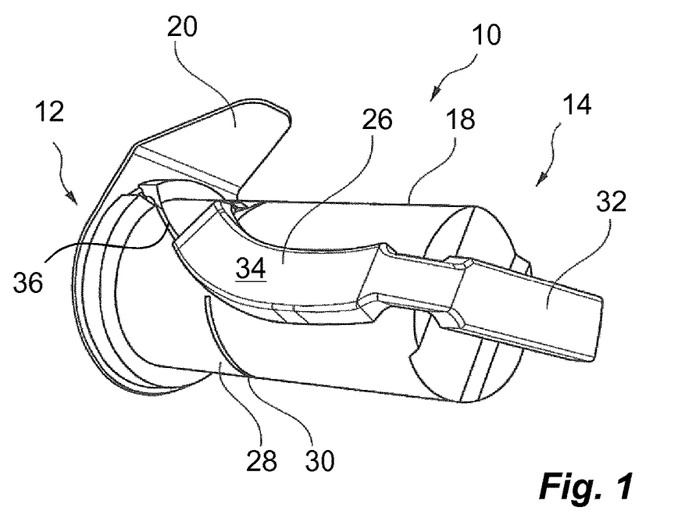
FIG. 1 shows a perspective view of a non-limiting example of a needle cover assembly, which may be used with a medicament delivery device.
Figure 2:
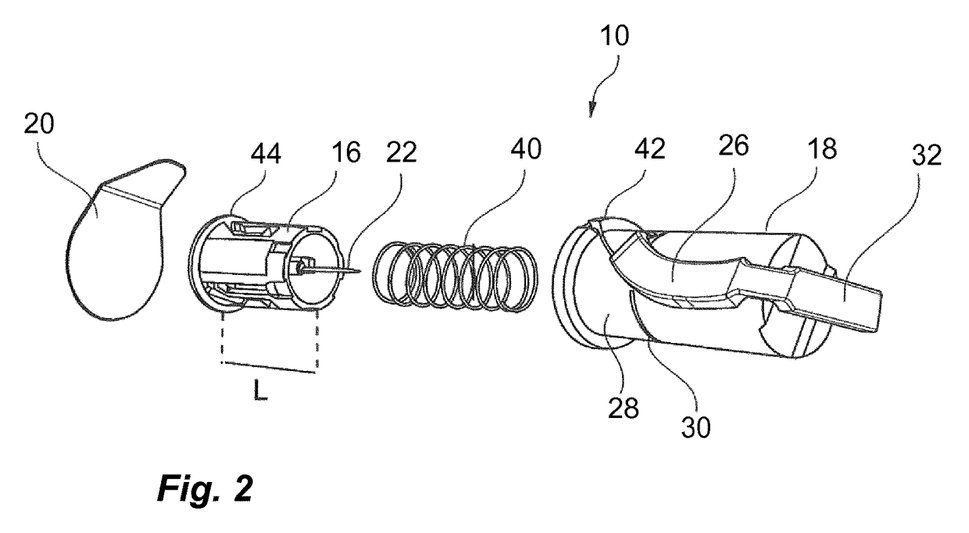
FIG. 2 shows an exploded view of the non-limiting example of the assembly of FIG. 1.
Figure 3A:
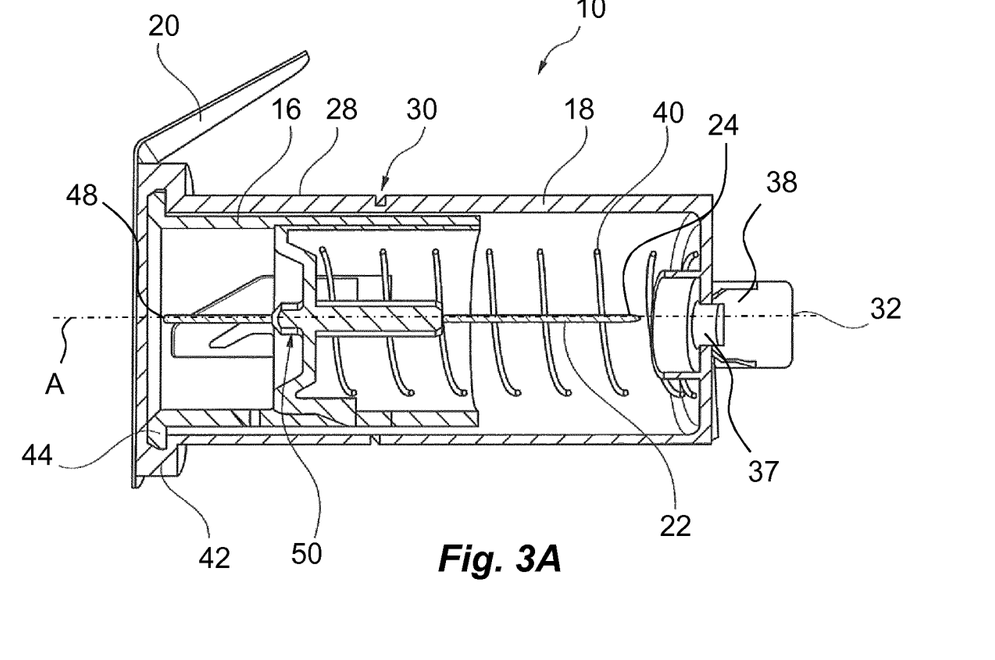
FIG. 3A shows a cross sectional view of a non-limiting example of a needle cover assembly in untampered state.

FIGS. 1 and FIG. 2 each show a disposable needle cover assembly 10 according to a first exemplary embodiment having a distal end 12 and a proximal end 14, said assembly being arranged to be used with a medicament delivery device for injection procedures. Referring mainly to FIGS. 1 and 2 the assembly 10 comprises, among other elements, a substantially cylindrical inner hub 16 covered by a substantially cylindrical outer shield 18 and a protective impermeable seal 20 such as a film, e.g. a protective label, removably attached onto and completely covering the distal open end of the shield 18. The hub 16 has a longitudinal axis A (shown in FIG. 4) and comprises a double pointed injection needle 22, wherein the proximal needle end 24 projects a distance from the hub 16 along the longitudinal axis A. FIG. 3A shows the assembly in an untampered state where the shield 18 encapsulates the proximal needle end 24 as well as the entire hub 16 thereby providing a protective cover, i.e. a protective cap. Together with the film 20 the shield 18 completely covers and protects the hub 16 and injection needle 22 and provides a sterile confinement as well as a container in which the device can be delivered to a consumer. This is also illustrated by the cross section of FIG. 3A.

The shield 18 further comprises a detachable element 26 which according to the embodiment seen in FIG. 1 comprises a removable portion 28 positioned towards the distal portion 12 of the assembly and arranged to be peelable from the shield 18 by a tearable or breakable, circumferentially extending line or groove 30 pre-arranged on the shield 18 surface as shown e.g. in FIGS. 1 and 2. A pull tab 32 may be integrated with the removable portion 28, for instance via a connecting bridge 34 as in FIG. 1 or as a direct prolonged portion of the detachable element 26. A further tearable groove 36 is arranged in the vicinity of connecting bridge 34 and is extending somewhat inclined in relation to the longitudinal axis A, as seen in FIG. 1.

Figure 3B:
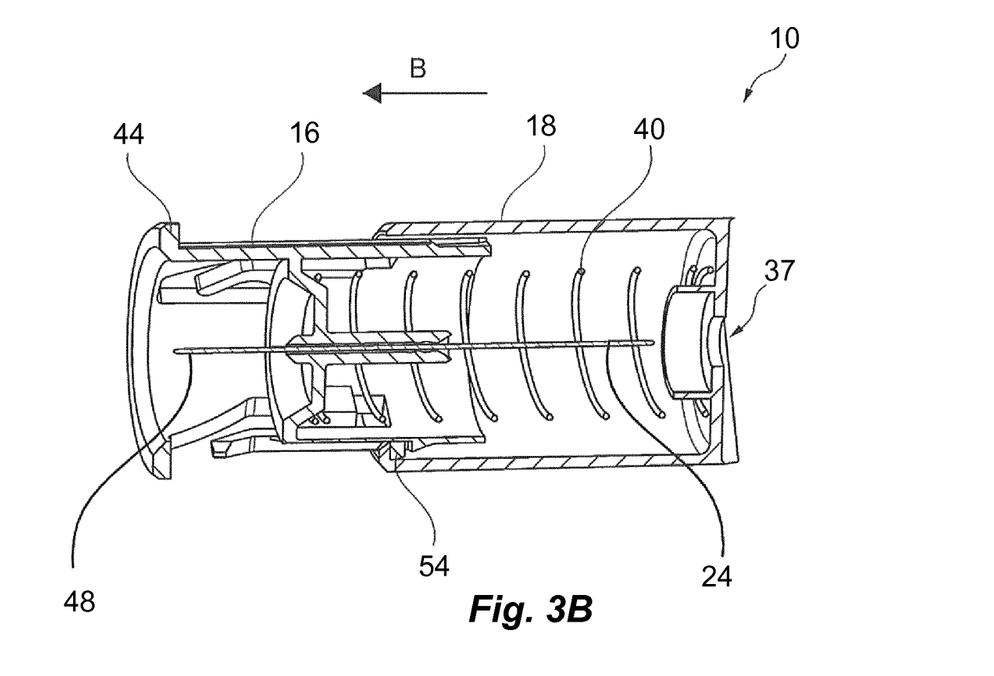
FIG. 3B shows a cross sectional view of a non-limiting example of a needle cover assembly in activated state.

Pulling the pull tab 32 results in breakage along both the inclined groove 36 as well as along the circumferential groove 30 so that the removable portion 28 is torn off, i.e. detached, thereby exposing a distal portion of the hub 16 as seen in FIG. 3B. The removable portion 28 is arranged on the shield 18 in such a way that when it is attached the shield 18 is movably attached to the hub 16, corresponding to the untampered state, whereas the shield 18 is telescopically movable in relation to the hub 16 along the longitudinal axis A when said removable portion 28 is detached/removed, corresponding to an activated state.

The substantially cylindrical shield 18 has a distal open end arranged to be impermeably sealed by said film or label 20, and a partially closed proximal end having a central opening 37, FIG. 3, with a diameter large enough for the needle to pass through. Before use, the central opening 37 is plugged by a removable needle seal 38, FIG. 3A. The needle seal 38 may be in the form of said pull tab 32 in which case it is connected to the removable portion 28 via the bridge 34, or it may be a separate, independent, plug element.

A resilient element 40, FIGS. 2 and 3, such as a compression spring is positioned between the hub 16 and the shield 18 and is arranged to urge the hub 16 and the shield 18 apart such that the shield 18 in activated state is urged to automatically move into a position where it covers the proximal end 24 of the injection needle 22. This means that the compression spring 40 will safeguard that the proximal needle end 24 will be covered by the shield 18 when the detachable element 26 is removed and the assembly 10 set to activated state leading to that the shield 18 is always urged to move into a proximal needle covering direction.

FIG. 3A shows a cross section of the assembly 10 in FIG. 1, wherein the shield 18 comprises said detachable element 26 at the distal portion of the shield and cooperates with said protective film 20 and the needle seal 38 to provide a sterile confinement, housing the hub 16, the injection needle 22 and the compression spring 40. In such untampered state the shield 18 is fixed in relation to the hub 16 and a distal flange 42 of the shield 18 is abutting and covering a corresponding distal flange 44 of the hub 16. As will be later described more thoroughly the shield 18 and the hub 16 are further interconnected via a guiding system 46, FIG. 4, which prevents the hub 16 and the shield 18 from sliding out of the telescopic engagement seen in FIG. 3A and also prevents uncontrolled rotational movements. Also the protective film 20 provides a certain contribution to stability of the assembly 10 and to that the different components are immobile in relation to each other before use.

In FIG. 3B the needle cover assembly 10 has been prepared for use, i.e. set to activated state wherein it is ready for injection. The protective film 20 as well as the needle seal 38 has been removed. Further, the detachable element 26 at the distal end 12 of the assembly 10 has been detached e.g. by peeling it off from the shield 18 thus exposing the distal portion of the hub 16 including the distal flange 44. A double pointed injection needle 22 is firmly attached to the hub 16 and extends through it along the longitudinal axis A. The injection needle 22 has a distal end 48 and a proximal end 24. The hub 16 is provided with a retainer element 50 at its distal end portion, FIG. 3A, facing the distal hub opening and provides a connection point, i.e. arranged to be connectable to a medicament delivery device 52 (see FIGS. 6-8). The retainer element 50 may be any conventional connection mechanism such as luer lock, bayonet or a threaded connection portion. In the activated state the shield 18 is telescopically movable in relation to the hub 16. This means, pushing the shield 18 in a distal direction B towards the distal flange 44 of the hub results in that the compression spring 40 will be tightened and the proximal needle end 24 will simultaneously extend through the central opening 37 of the shield 18.

Figure 4:
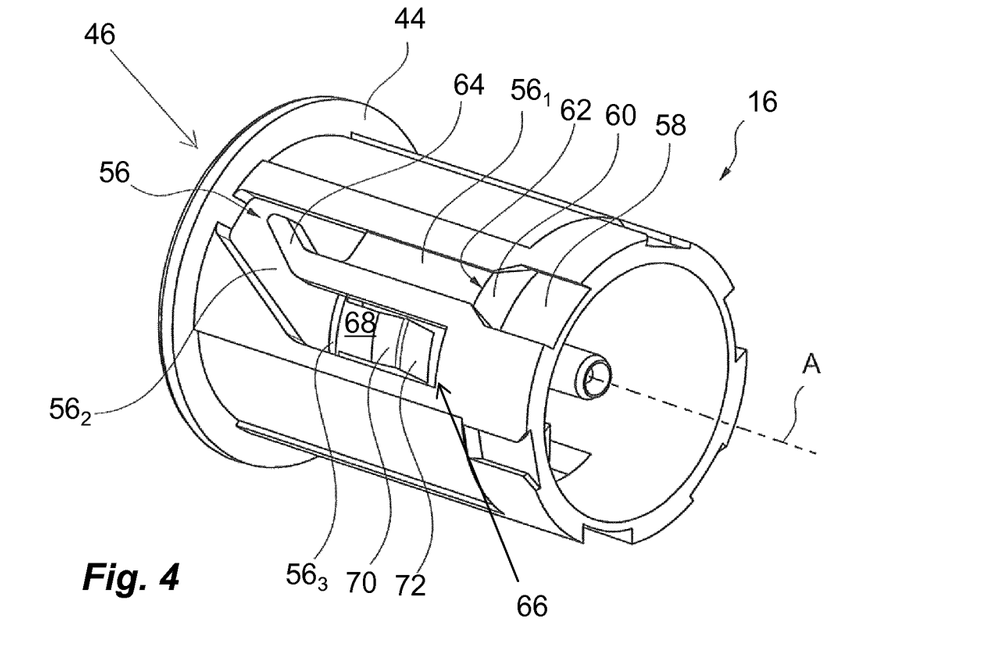
FIG. 4 shows a perspective view of a non-limiting example of a hub.
Figure 5:
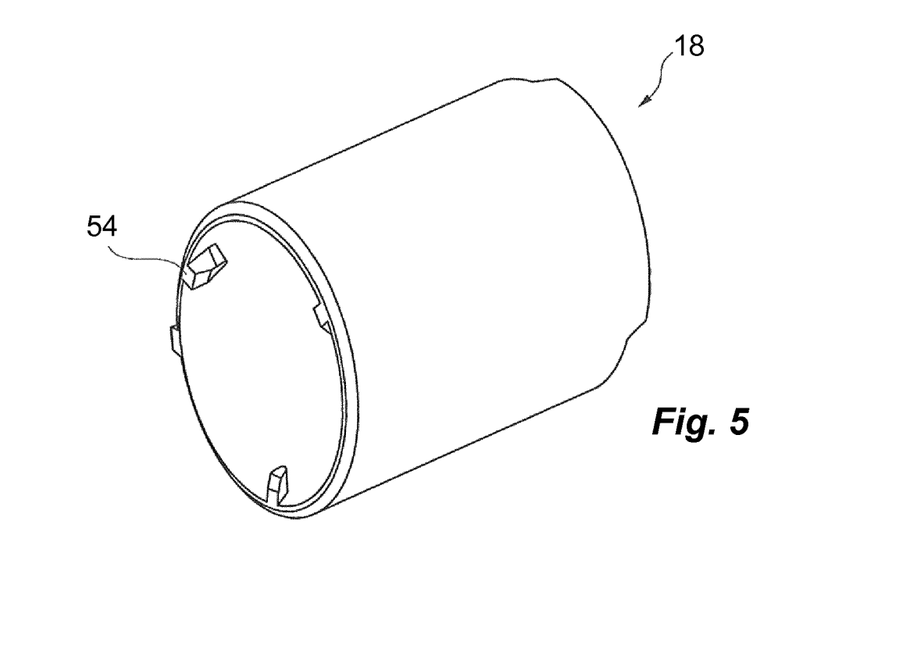
FIG. 5 shows a perspective view of a non-limiting example of a shield.

The shield 18 and the hub 16 are engaged with each other via the guiding system 46 by means of which the shield 18 is guided along the outside surface of the hub 16 so that it in an activated state is telescopically movable in relation to said hub. Referring mainly to FIG. 4 and FIG. 5, the shield 18 is slidably engaged with the hub 16 by means of inwardly directed projections 54 as shown in FIG. 5, arranged to be guided in guiding slots 56 provided on the hub 16 as shown in FIG. 4. In the example shown in FIGS. 4-5, the shield 18 is designed with a number of three projections 54, and the hub 16 consequently has three guiding slots 56 for receiving and guiding the projections 54. Obviously, the number of projections 54 and corresponding guiding slots 56 may vary and is not limited by the example given herein.

FIG. 4 shows a perspective view of a hub 16 according to one embodiment, comprising an example of a guiding slot 56 positioned substantially longitudinally along the body of the hub 16 allowing for longitudinal telescopic movement of the shield 18. The guiding slot 56 comprises a first longitudinally extending portion $56_1$, a second portion $56_2$ connected to the first portion $56_1$ at an acute angle, and a third longitudinally extending portion $56_3$ connected to the second portion $56_2$.

The first $56_1$ and the third portions $56_3$ may be arranged to be parallel to each other, i.e. along the longitudinal axis A, however it is also conceivable to arrange the third portion $56_3$ as an angled continuation of the second portion $56_2$.

Each guiding slot 56 commences with an insertion groove 58 arranged at the proximal end of the hub 16. The insertion grooves 58 serve the purpose of simplifying connection of the shield 18 and the hub 16 during manufacturing: i.e. the hub 16 is inserted into the shield 18 by firstly sliding the projections 54 into the insertions grooves 58 and further over an inclined surface 60 which ends at a steep stopping edge 62. Upon assembling the assembly 10, the projections 54 of the shield 18 will be moved into the insertions grooves 58, after which they are urged to climb said inclined surface 60 until reaching the top where they snap down at the stopping edges 62. At this point the shield 18 and the hub 16 are irreversibly connected to each other and the projections 54 can no longer slide out of the guiding slot 56.

Said stopping edge 62 is located at the proximal end of the first portion $56_1$ of the guiding slot 56. As previously described, the stopping edge 62 provides a stop for a corresponding projection 54 and prevents the projection 54 once located in the guiding slot 56 from sliding out of it. The stopping edge 62 may be in the form of a stopping edge against which edge the projections 54 are resting when the assembly 10 is in neutral state and the compression spring 40 pushes the shield into a needle covering position.

An elastically deformable safety element 64 is located between the first $56_1$ and the second $56_2$ portion of the guiding slot 56, and is designed to permit passage of a projection 54 which is guided in the guiding slot 56 in a direction from said first portion $56_1$ to said second portion $56_2$, while preventing passage in the opposite direction, i.e. in a direction from said second portion $56_2$ to said first portion $56_1$. The safety element 64 may be designed as a projecting, elastically deformable tongue designed so that when pressed in a distal direction it will bend to open up a wider passage between the first $56_1$ and second $56_2$ portion, but flex back so as to close the passage when subjected to pressure in the opposite, proximal direction. In one example this is accomplished by means of said elastically deformable safety element 64 being arranged to project at an angle in relation to the longitudinal axis A, pointing towards said first portion $56_1$.

The third portion $56_3$ of the guiding slot 56 is arranged with a locking element 66 providing the function of engaging a projection 54 and irreversibly locking it in relation to the hub 16. Such locking function can be achieved in various ways. According to the example in FIG. 4, the locking element 66 comprises a tongue 68 directed in the proximal direction and flexible in the generally radial direction, wherein the free end of the tongue is arranged with a wedge-shaped elevation 70 ending in a steep edge 72 which, in its turn, faces the proximal direction. A projection 54 which is guided towards the locking element 66 will firstly climb the wedge-shaped elevation 70 wherein the tongue 68 is flexing radially inwards and thereafter, upon passing by the steep edge 72, snap into a permanently locked position wherein the tongue 68 flexes back to its original position.

Figure 6A:
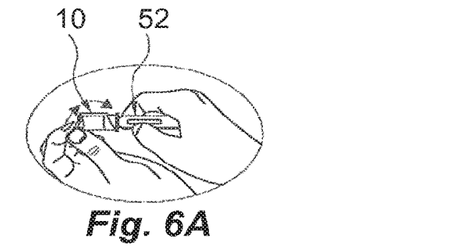
FIGS. 6A-B show examples of using a non-limiting first example of the needle cover assembly.
Figure 6B:
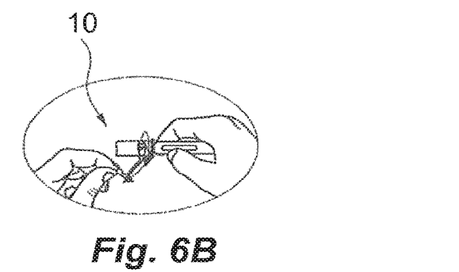
Figure 7A:
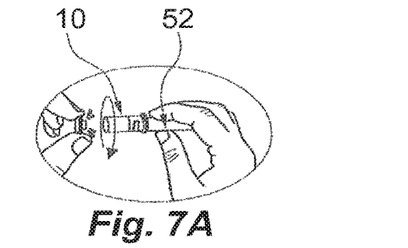
FIGS. 7A-B show examples of using a non-limiting second example of the needle cover assembly.
Figure 7B:
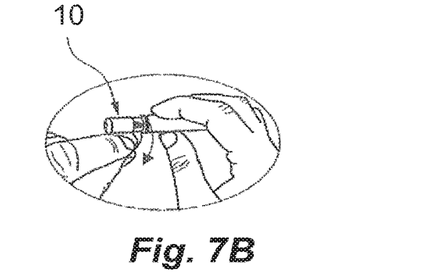

Preparing the needle cover assembly 10 for injection is now to be described. FIGS. 6A and 6B illustrate use of a first embodiment and FIGS. 7A and 7B illustrate use of a second embodiment of a needle cover assembly 10.

Figure 8:
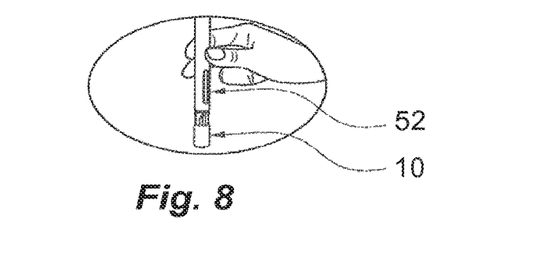
FIG. 8 shows the needle cover assembly in activated state connected to a medicament delivery device ready for injection.

The needle cover assembly 10 is delivered to a user in an untampered state, as seen e.g. in FIG. 1. The shield 18 then acts as a sterile container sealed by said protective film 20. As a first step of use, the label is removed from the assembly 10 to expose the retainer element 50 of the hub 16 and permitting attaching the assembly 10 onto a medicament delivery device 52 which is loaded with a medicament containing cartridge. Such attachment can be accomplished by means of connection via luer lock, bayonet, threads or any other conventional method. During connection, the distal needle end 48 of the injection needle 22 will pierce the cartridge and contact the liquid medicament inside. FIGS. 6-8 each shows an assembly 10 already attached onto a medicament delivery device 52.

The shield 18 is thereafter transformed from a protective cap into a functional needle safety guard by pulling off the detachable element 26, which will get the assembly 10 to adopt an activated state in which it is ready for injection. In the following, two non-limiting solutions are presented using two alternative embodiments: a first embodiment in FIGS. 6A-B and a second in FIGS. 7A-B. The first embodiment (6A-B) has a needle seal 38 outlined as a pull tab integrated with the removable portion 28 of the shield 18 via a connecting bridge 34, see FIG. 1, whereas in the second embodiment the needle seal 38 is a separate unit, i.e. it is not connected with the removable portion 28.

According to a first embodiment, FIG. 6A, a user prepares the assembly for injection by removing the needle seal 38 which plugs the central opening 37 at the distal front of the shield 18. The needle seal 38 of the first embodiment is designed as a pull tab 32 which is connected to a removable portion 28 which is integral with the shield 18 and is located towards the distal end 12 of the assembly 10. Pulling the pull tab 32 both leads to removal of the needle seal 38 and to peeling off the removable portion 28 in one continuous movement, see FIG. 6B. Once the detachable element 26 is removed from the shield 18, the assembly 10 is set to an activated state wherein the shield 18 is telescopically movable in relation to the hub 16. In an activated, neutral state the compression spring 40 presses the shield in a proximal direction so that the inner projections 54 rest against the stopping edge 62 of the hub 16, corresponding to a needle covering position.

When preparing the second embodiment, FIG. 7A, for injection a user removes the needle seal 38 in one step and peels off the removable portion 28, in another independent step. As seen in FIG. 7A the needle seal 38 can be twisted off from the shield 18 uncovering the central opening 37, however it is equally conceivable that the needle seal is yet another pull tab or a label or any other suitable sealing element. The removable portion 28 of the second embodiment has a pull tab 32 for simplifying gripping. FIG. 7B illustrates the step of peeling off the removable portion 28 from an assembly 10 according to a second embodiment. The user grips the pull tab and peels off the spiral wound portion from the shield uncovering the distally located end of the hub 16.

The needle cover assembly 10 is now ready for injection, as illustrated in FIG. 8.

During an injection procedure the shield 18 will be guided along the outside surface of the hub 16 by said guiding system 46. The function of the guiding system 46 will now be further described, referring mainly to FIGS. 9A-C schematically showing the relation between the shield 18 and the hub 16 during an imaginary injection: in reality the assembly 10 is for instance attached to a medicament delivery device 52 whereas in FIG. 9A-C it is shown as an isolated unit.

Figure 9A:
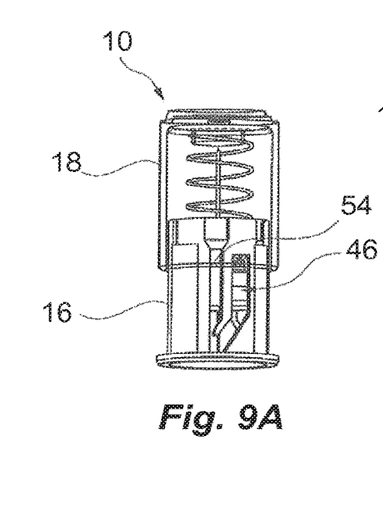
FIGS. 9A-C show in a non-limiting way the function of an exemplary guiding system and the needle cover assembly in different positions before, during and after injection.
Figure 9B:
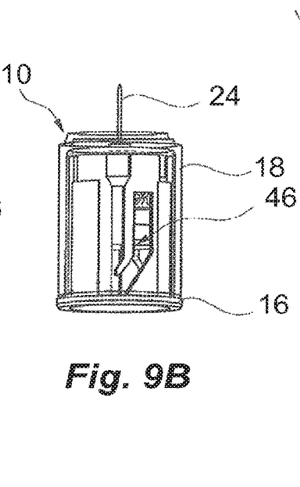
Figure 9C:
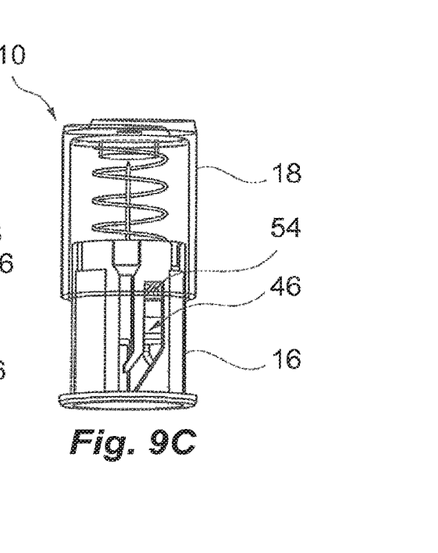

Starting with FIG. 9A, the needle cover assembly 10 is seen in an activated state in a start position before injection is initiated. The telescopically movable shield 18 is urged by the compression spring 40 to a maximal extended configuration wherein the inwardly directed projections 54 are pressed in a proximal direction onto the stopping edge, at the first portion $56_1$, see FIG. 4, of the guiding slot 56. The shield 18 thus covers the proximal needle end 24 preventing unintentional needle sticks, and the shield is kept in the extended configuration regardless of orientation until injection is commenced.

Injection may be initiated by pressing the proximal front end of the shield 18 against a delivery site on a patient's body. This will cause the compression spring 40 to compress and the assembly to collapse so that the injection needle 22 extends through the central opening 37 and pierces the skin of the patient. During this movement the shield 18 is guided by the guiding system 46 along the outside surface of the hub 16. The projections 54 slide along the first longitudinally extending portion $56_1$ of the guiding slot 56 towards the distal end 12 of the assembly 10 and will pass by said elastically deformable safety element 64 which upon passage of a projection firstly will yield to permit passage and then snap back preventing the projection 54 from returning to the start position. The distal edge of the shield 18 will eventually be stopped when abutting the distal flange 44 of the hub, in which position the assembly 10 is fully collapsed as seen in FIG. 9B. In this injection position the proximal needle end 24 is fully inserted into the patient's body for delivering an injection. The projections 54 are now at the second portion $54_2$ of the guiding slot 56.

Upon completion of injection, the user will start removing the assembly 10 from the body. As soon as it is released from outer pressure, the compression spring 40 will expand urging the shield 18 towards a proximal direction for covering the needle 22 as it is retracted from the skin. As the shield 18 moves in said proximal direction, the projections 54 are sliding along the second portion $56_2$ having an acute angle, leading to that the shield 18 is slightly rotated in relation to the hub 16. When approaching a maximal extended configuration the projection 54 will be brought into the last, third portion 56₃ of the guiding slot 56 where it engages the locking element 66 and becomes permanently locked in an end position, shown in FIG. 9C.

It is to be understood that the embodiment described above and shown in the drawings is to be regarded only as a non-limiting example of the invention and that it may be modified in many ways within the scope of the patent claims.

For instance, other ways of achieving the safety function of said elastically deformable safety element 64 are conceivable, such as elevations and cooperating stopping edges or snap-in solutions.

The invention claimed is:

1. A needle cover assembly configured to be used with a medicament delivery device, wherein the needle cover assembly comprises:
    a retainer element connectable to a medicament container holder,
    a hub having a longitudinal axis and comprising a double pointed injection needle with a proximal needle end and a distal needle end,
    wherein the proximal needle end projects from the hub along the longitudinal axis,
    a shield covering the proximal needle end and a portion of the hub, the shield comprising a proximal central opening on the longitudinal axis,
    a needle seal positioned within and blocking the proximal central opening in an untampered state,
    a detachable element comprising (i) a removable portion at a distal end of the needle cover assembly that is integral with the needle seal and (ii) a pull tab, wherein the detachable element is configured such that pulling on the pull tab can result in (a) peeling off the removable portion from the shield, thereby detaching the detachable element from the shield and (b) removing the needle seal from within the proximal central opening,
    wherein in the untampered state the removable portion of the shield is attached to a distal end of the hub, thereby preventing the shield from moving telescopically in relation to the hub, and
    wherein in an activated state the shield is released via removal of the removable portion from the distal end of the hub and the shield is telescopically movable in relation to the hub via removal of the removable portion,
    wherein the removable portion is removable from the distal end of the hub via breakage at a circumferential groove that defines a plane that is perpendicular to the longitudinal axis and via breakage at an inclined groove that intersects a distal flange of the shield and the circumferential groove.

2. The needle cover assembly according to claim 1, wherein the detachable element is an integral part of the shield.

3. The needle cover assembly according to claim 1, wherein the shield in the untampered state is arranged to cover the injection needle.

4. The needle cover assembly according to claim 3, wherein the shield in the untampered state is arranged to cover a length of the hub.

5. The needle cover assembly according to claim 1, further comprising a protective impermeable seal arranged to cooperate with the shield in the untampered state to seal the hub and the injection needle in a sterile manner.

6. The needle cover assembly according to claim 1, further comprising a resilient element positioned between the hub and the shield.

7. The needle cover assembly according to claim 6, wherein the resilient element is arranged to urge the hub and the shield apart.

8. The needle cover assembly according to claim 7, wherein the resilient element is arranged to urge the hub and the shield apart such that the shield, when in the activated state, is urged to move into a position where the shield covers the proximal end of the injection needle.

9. The needle cover assembly according to claim 1, further comprising a guiding system wherein the shield is guided along an outside surface of the hub and is telescopically movable in a longitudinal direction in relation to the hub.

10. The needle cover assembly according to claim 9, wherein the guiding system comprises:
    an inwardly directed projection provided on the shield, and
    a guiding slot on the hub,
    wherein the projection is arranged to be guided in the guiding slot.

11. The needle cover assembly according to claim 10, wherein the guiding slot is arranged with a first longitudinally extending portion, a second portion connected to the first portion at an acute angle, and a third portion connected to the second portion.

12. The needle cover assembly according to claim 11, further comprising a locking element configured for engaging the projection and locking the shield in relation to the hub.

13. The needle cover assembly according to claim 11, further comprising a locking element for engaging the projection and irreversibly locking the shield in relation to the hub.

14. The needle cover assembly according to claim 11, wherein the guiding system further comprises an elastically deformable safety element located between the first portion and the second portion of the guiding slot, the safety element being arranged to permit passage of the projection which is guided in the guiding slot in a direction from the first portion to the second portion.

15. The needle cover assembly according to claim 14, wherein the safety element is configured to prevent passage of the projection which is guided in the guiding slot in a direction from the second portion to the first portion.

16. The needle cover assembly according to claim 11, wherein the guiding system comprises a stopping edge located at a proximal end of the first portion of the guiding slot,
    the stopping edge providing a stop for the projection and preventing the projection once located in the guiding slot from sliding out of the guiding slot.

17. The needle cover assembly according to claim 1, wherein the shield and the hub in the activated state can be shifted between a plurality of locations during an injection procedure, the positions comprising:
    an initial position prior to injection where the shield fully covers the proximal needle end and a proximal end portion of the hub,
    an active position during injection where the shield is moved in a distal direction thus tightening a resilient element and exposing the proximal needle end for penetrating a body, and an end position where the shield is pushed by the resilient element to an irreversibly locked state fully covering the proximal needle end.

18. The needle cover assembly according to claim 1, wherein a distal flange of the removable portion covers a distal flange of the hub in the untampered state.

19. A medicament delivery device comprising a housing having a longitudinal axis and a medicament container holder for receiving a container with a medicament, the medicament delivery device further comprising the needle cover assembly according to claim 1.

\* \* \* \* \*